US006232786B1

(12) United States Patent
Barnett (10) Patent No.: US 6,232,786 B1
(45) Date of Patent: May 15, 2001

(54) APPARATUS AND METHOD FOR MEASURING CONDUCTIVITY (75) Inventor: Ben E. Barnett, Beavercreek, OH (US)

(73) Assignee: YSI Incorporated, Yellow Springs, OH (US)

( * ) Notice: Subject to any disclaimer, the term of this patent is extended or adjusted under 35 U.S.C. 154(b) by 0 days.

(21) Appl. No.: 09/284,036

(22) PCT Filed: Sep. 25, 1997

(86) PCT No.: PCT/US97/17237

§ 371 Date: Jun. 7, 1999

§ 102(e) Date: Jun. 7, 1999

(87) PCT Pub. No.: WO98/14689

PCT Pub. Date: Apr. 9, 1998

Related U.S. Application Data (60) Provisional application No. 60/027,327, filed on Oct. 3, 1996.

(51) Int. Cl.⁷ ............................ G01R 27/08; G01N 27/02
(52) U.S. Cl. ......................... 324/691; 324/441; 324/442; 324/444
(58) Field of Search .................................... 324/691, 442, 324/444, 441

(56) References Cited

U.S. PATENT DOCUMENTS

| 3,757,205 | * | 9/1973 | Dauphinee | 324/444 |
| 3,849,723 | * | 11/1974 | Allen | 424/435 |
| 3,906,353 | | 9/1975 | Murdock | 324/442 |
| 3,982,177 | * | 9/1976 | Walker et al. | 324/442 |
| 4,262,253 | | 4/1981 | Clark | 324/439 |
| 4,383,221 | * | 5/1983 | Morey et al. | 324/441 |
| 4,491,798 | | 1/1985 | Palmer et al. | 324/425 |
| 4,511,845 | * | 4/1985 | Dauphinee et al. | 204/242 |
| 4,751,466 | | 6/1988 | Colvin et al. | 324/449 |
| 4,808,930 | | 2/1989 | Kaiser | 324/442 |
| 4,825,168 | * | 4/1989 | Ogawa et al. | 324/442 |
| 5,057,772 | | 10/1991 | Bruno et al. | 324/754 |
| 5,260,663 | | 11/1993 | Blades | 324/442 |
| 5,334,940 | * | 8/1994 | Blades | 324/442 |
| 5,455,513 | | 10/1995 | Brown et al. | 324/445 |
| 5,543,717 | | 8/1996 | Kordas | 324/444 |
| 5,677,190 | * | 10/1997 | Melanson et al. | 422/78 |

OTHER PUBLICATIONS

Jones, G. et al., "The Measurement of the Conductance of Electrolytes," *Journal of the American Chemical Society*, vol. 50, Apr. 1928, pp. 1049–1092.

(List continued on next page.)

*Primary Examiner*—Safet Metjahic
*Assistant Examiner*—Wasseem H. Hamdan
(74) *Attorney, Agent, or Firm*—Biebel & French (57) ABSTRACT An improved apparatus for measuring conductivity or resistivity compensates for series capacitance and parallel capacitance. A sine wave excitation potential is applied to the series combination of a reference resistance and a conductivity cell. The voltages across the reference resistance and the cell are sampled. To compensate for series capacitance, both sampled voltages are synchronously rectified with respect to the phase of the sampled reference resistance voltage. To compensate for parallel capacitance, both sampled voltages are synchronously rectified with respect to the phase of the sampled cell voltage. The rectified voltages are integrated and the cell conductivity or resistivity is calculated from the product of the reference resistance and the ratio of the integrated voltages.

9 Claims, 7 Drawing Sheets

OTHER PUBLICATIONS

Jones, G. et al., "The Measurement of the Conductance of Electrolytes," *Journal of the American Chemical Society*, vol. 51, Aug. 1929, pp. 2407–2416.

Shedlovsky, T., "A Screened Bridge for the Measurement of Electrolytic Conductance," *Journal of the American Chemical Society*, vol. 52, May 1930, pp. 1793–1805.

Jones, G. et al., "The Measurement of the Conductance of Electrolytes," *Journal of the American Chemical Society*, vol. 53, Apr. 1931, pp. 1207–1212.

Dike, P.H., "A Bridge for the Measurement of the Conductance of Electrolytes," *Review of Scientific Instruments*, vol. 2, Jul. 1931, pp. 379–395.

Janz, G.J. et al., "A Precision Conductance Bridge of New Design," *Journal of the Electrochemical Society*, vol. 108, No. 3, Mar. 1961, pp. 272–276.

* cited by examiner

APPARATUS AND METHOD FOR MEASURING CONDUCTIVITY

This application claims benefit of 60/027,327, filed Oct. 3, 1996, and this application is a 371 of PCT/US97/17237, filed Sep. 25, 1997.

BACKGROUND OF THE INVENTION

1. Field of the Invention

This invention relates to an improved apparatus and method for measuring electrical conductivity or resistivity in liquids, and more particularly, it relates to a conductivity measuring apparatus having a phase-synchronous rectifier and integrator for accurately measuring electrical conductivity in the presence of parasitic capacitance.

2. Background of the Invention

The measurement of conductivity or resistivity is desired in a number of applications. For example, in the pharmaceutical industry, many processes require the use of ultra-pure water. Conductivity measurements yield an indication of ionic concentrations in water. Ultra-pure water has a conductivity below a given level. Conductivity measurements can therefore be used to reliably and accurately determine the purity of water.

Another application where it is desirable to measure the conductivity of a liquid is the determination of the concentration of total dissolved solids in water. For example, investigators desiring to determine the level of pollution in river water want to know the concentration of total dissolved solids in the water. The higher the concentration of total dissolved solids in the water, the higher the conductivity, or inversely, the lower the resistivity of the water.

The volume conductivity, or just "conductivity", is defined as the conductance of one cubic centimeter of a liquid at a specific temperature. Conductivity is typically measured in mhos/cm (℧/cm), or Siemens/cm (S/cm), and micro mhos/cm (μ℧/cm), or micro Siemens/cm (μS/cm). Ultra-pure water typically has a conductivity of 0.2 micro mhos/cm or less. Volume resistivity ("resistivity") is the inverse of conductivity and is typically measured in ohm-cm (Ω-cm), or megohm-cm (MΩ-cm). Ultra-pure water typically has a resistivity of 5 megohms-cm or greater.

Conductivity of a liquid is typically measured by immersing two electrodes contained in a conductivity cell in the liquid, applying an excitation to the liquid, and measuring the resultant voltage $v_c$ between the electrodes and the current $i_c$ flowing through the electrodes. Because a direct current ("DC") excitation can cause ions present in the liquid to migrate to the electrodes, interfering with the conductivity measurement, an alternating current ("AC") excitation of sufficiently low amplitude and sufficiently high frequency is often used.

Measurements of conductivity and resistivity vary depending upon the cell used to make the measurements, the temperature of the liquid being measured, and the concentration of ions or other electrically conductive material in the liquid. A cell with fixed dimensions and configuration is typically used. For a given fixed cell, a cell constant K may be defined as a function of conductive cell surface area and conductive path length For a cell with two flat parallel plates of area A and separation distance L, the cell constant K is found to be the length L of the conductive path between the electrodes, divided by the conducting area A of the electrodes, so that K=L/A.

For a given cell, the conductivity and resistivity of a liquid are then given by $$\sigma = \frac{K i_c}{v_c} \quad \text{(eq. 1)}$$

and $$\rho = \frac{1}{\sigma} = \frac{v_c}{K i_c} \quad \text{(eq. 2)}$$

Where:
$i_c$=the electric current flowing between the cell electrodes, in Amperes,
$v_c$=the voltage across the cell electrodes, in Volts, and
K=the cell constant, in cm$^{-1}$.

The conductivity cell immersed in liquid may be electrically modeled as a resistor $R_c$ with value equal to the resistivity ρ times the cell constant K, such that $$R_c = K\rho. \quad \text{(eq.3)}$$

Figure 1:
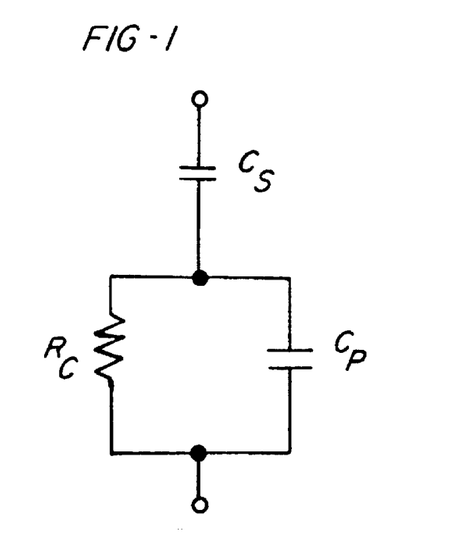
FIG. 1 is an electrical schematic of a conductivity cell immersed in a liquid.

However, accurate measurement of $R_c$ is difficult when an AC excitation is used due to capacitive effects of the cell, as well as capacitive effects of the lead wires to the cell. At the interface between each cell electrode and the liquid is a series capacitance $C_S$. Between each electrode is a capacitance in parallel with the resistance $R_c$, represented by $C_p$. Including the capacitive effects, the cell may be electrically modeled as a parallel capacitance $C_p$ in parallel with liquid resistance $R_c$, both in series connection with series capacitance $C_s$, as shown in FIG. 1. Lead wire cabling capacitance (not shown) would appear as a capacitance in parallel across the circuit of FIG. 1.

The cell capacitances $C_p$ and $C_s$ exhibit impedances to an AC excitation which vary inversely as a function of the excitation frequency f (measured in cycles/second or Hertz). For a relatively low frequency f, the impedances of $C_p$ and $C_S$ can be quite large for fixed values of $C_p$ and $C_s$. For small values of $R_c$, the impedance of series capacitance $C_s$ can be large compared to $R_c$, thus giving rise to an erroneously large measured value for $R_c$. For large values of $R_c$, the impedance of parallel capacitance $C_p$ can be small relative to $R_c$, thus giving rise to erroneously small measured values of $R_c$.

For a relatively high excitation frequency f the impedances of $C_p$ and $C_s$ can be quite small for fixed values of $C_p$ and $C_s$. For small values of $R_c$, the impedance of series capacitance $C_s$ can be large compared to $R_c$, thus giving rise to an erroneously large measured value for $R_c$. For large values of $R_c$, the impedance of parallel capacitance $C_p$ can be small relative to $R_c$, thus giving rise to an erroneously small measured value for $R_c$.

In general, at a given frequency f and fixed $C_s$ and $C_p$, as the resistivity of a sampled liquid increases, the impedance due to series capacitance $C_s$ can be ignored, while the impedance of parallel capacitance $C_p$ causes an erroneously small value for $R_c$ to be measured. Conversely, as the resistivity of a sampled liquid decreases, the impedance due to parallel capacitance $C_p$ can be ignored, while the impedance of series capacitance $C_s$ causes an erroneously large value for $R_c$ to be measured.

Thus, for large values of cell resistance $R_c$, the measurement error is largely due to the presence of parallel capacitance $C_p$. For small values of cell resistance $R_c$, the primary source of measurement error is due to the presence of series capacitance $C_s$.

Various efforts to measure conductivity in the presence of capacitive effects are known in the prior art. An early method uses an AC conductance bridge, wherein different reactances are inserted into the arms of the bridge to compensate either or both $C_s$ and $C_p$. While this method is effective, it is generally slow and not easily automated.

Another measurement technique uses square-wave excitation and center-sampling of the voltage waveform across the cell. The parallel capacitance is charged to saturation during the first part of the square-wave cycle. The cell voltage is then sampled during a later portion of the cycle during which the series capacitance is charging in a linear fashion. The value of the series capacitance can be determined from the rate of charge of the capacitance and mathematically subtracted from the output based on the cell voltage to determine the cell resistance. This measurement technique suffers from the disadvantage of relying upon the use of a second-order polynomial to approximate the amount of measurement error. Thus, this prior art method does not eliminate the source of error itself, the voltage due to the series capacitance.

SUMMARY OF THE INVENTION

These disadvantages and others are met by means of the present invention embodied in a circuit and method for measuring the conductivity sensed by a cell wherein the effects of series and parallel capacitance inherent in cells are mined.

In the present invention, a periodic time-varying excitation is applied across a known reference resistance series-connected to a cell sensor. The voltages across the reference resistance and the cell sensor are synchronously sampled with respect to a predetermined signal phase. The synchronous sampled voltages are then integrated with respect to a predetermined signal phase to provide DC values representative of their RMS values. By sampling and integrating the signals synchronously, voltage components due to cell capacitance are substantially eliminated, leaving the voltage components due to cell resistance. The cell resistance is then found as a product of the reference resistance and the ratio of the RMS value of the synchronous sampled cell signal to the RMS value of the synchronous sampled reference resistance voltage.

Therefore, it is one object of the invention to provide a measurement of the conductivity of liquids reliably and accurately, even when parasitic cell capacitances are present. This and other objects, features and advantages of the present invention will be described in further detail in connection with preferred embodiments of the invention shown in the accompanying drawings, wherein:

DETAILED DESCRIPTION OF THE PREFERRED EMBODIMENTS

As discussed above, the resistance of a liquid the conductivity of which is desired is not an ideal resistance. As shown in FIG. 1, a conductivity cell immersed in a liquid may be modeled as a cell resistance $R_c$ in parallel with a capacitance $C_p$, both in series with a capacitance $C_s$.

Series capacitance $C_s$ is caused by liquid-electrode interface capacitance and is a function of the resistivity of the liquid under measurement and the available surface area of the cell electrodes. Values for series capacitance $C_s$ typically range from as low as 0.1 µF to in excess of 100 µF. For example, platinum electrodes plated with highly porous platinum black generally have $C_s > 1$ µF, while titanium-palladium electrodes may typically have $C_s \approx 0.1$ µF.

Parallel capacitance $C_p$ is caused by interelectrode capacitance, which is a function of cell geometry and electrode separation distance, as well as lead wire cabling capacitance. Cabling capacitance can dominate interelectrode capacitance by a factor often times or more. Values for $C_p$ typically may vary from a low of 10 pF to a high of 2500 pF.

For large values of resistance $R_c$, the principal source of measurement error is due to the presence of parallel capacitance $C_p$ while measurement error due to the presence of series capacitance $C_s$ may be ignored. For small values of resistance $R_c$, the principal source of measurement error is due to the presence of series capacitance $C_s$ while measurement error due to the presence of parallel capacitance $C_p$ may be ignored.

By way of illustration, assume typical values for $C_s$ and $C_p$ such that $C_s = 1$ µF and $C_p = 600$ pF. At a driving frequency f=70 Hz, $C_s$ and $C_p$ will exhibit reactances $X_s$ and $X_p$ given by $$x = \frac{1}{2\pi fC} \qquad (eq.\ 4)$$

such that $X_c = 2.274$ kΩ and $X_p = 3.789$ MΩ. The measured cell resistance $R_m$ will then be given by $$R_m = X_s + X_p \| R_c = X_s + \frac{1}{\frac{1}{R_c} + \frac{1}{X_p}}. \qquad (eq.\ 5)$$

For the given values, and a required degree of accuracy, a range of values for which $R_m$ exhibits the required degree of accuracy for $R_c$ can be determined. In this example, for a required measurement accuracy of ±0.25%, the range over which $R_c$ may be accurately measured extends from a low value of $R_c \approx 89.18$ kΩ to a high value of $R_c \approx 99.01$ kΩ, with minimal error at $R_c \approx 93.96$ kΩ.

Figure 2:
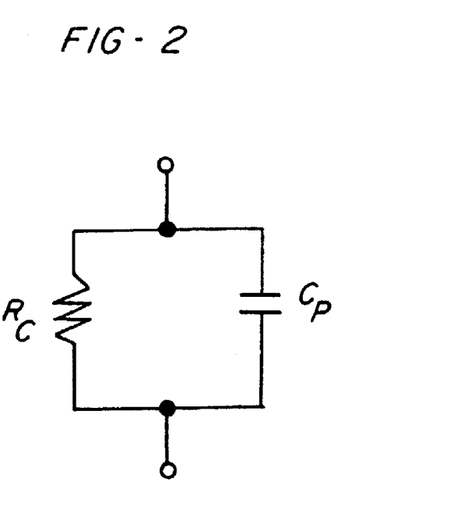
FIG. 2 is an electrical schematic of a conductivity cell immersed in a liquid modeled as a parallel RC circuit.

Now, assuming that $R_c$ and $X_p$ are much larger than $X_s$ ($R_c \gg X_s$ and $X_p \gg X_s$), the electrical model of FIG. 1 can be approximated by the simple parallel circuit of $R_c$ in parallel with $C_p$, as shown in FIG. 2. Provided that some means can be used to substantially compensate the effect of the parallel capacitance $C_p$, then the accuracy of the measurement of $R_c$ is limited only by the presence of $C_s$. For example, the measured resistance $R_m$ as given above reduces to $$R_m = X_s + R_c. \qquad (eq.\ 6)$$

Thus, for a required accuracy of +0.25%, the range for $R_c$ now extends from a low value of $R_c \approx 909.6$ kΩ to an arbitrarily large value limited only by the sensitivity of the measurement apparatus. For these large values of $R_c$, $R_c \geq 400 X_s$, and $X_p \geq 1600 X_s$, thus verifying the assumptions that $R_c >> X_s$ and $X_p >> X_s$ are valid. Therefore, large values of cell resistance can be accurately measured using a parallel capacitance model, provided that some means is used to substantially compensate the effects of parallel capacitance $C_p$.

Figure 3:
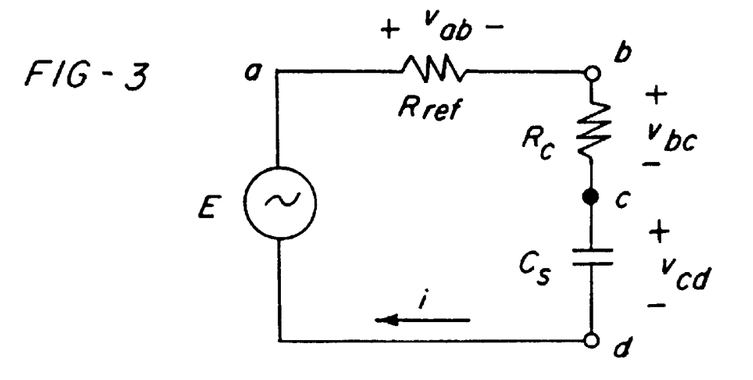
FIG. 3 is an electrical schematic of a conductivity measuring circuit modeled as a series circuit.

The inventor has observed that for the series model shown in FIG. 3, $$v_{ab} = iR_{ref} \qquad (eq.\ 7)$$

and $$v_{bd} = v_{bc} + v_{cd} = iR_c + v_{cd}. \qquad (eq.\ 8)$$

If both sides of the equations are integrated, then $$\int v_{ab} dt = R_{ref} \int i\, dt \qquad (eq.\ 9)$$

and $$\int v_{bd} dt = R_c \int i\, dt + \int v_{cd} dt. \qquad (eq.\ 10)$$

Solving for $\int i\, dt$ in eq. 9 and substituting the result in eq. 10, then $$\int v_{bd} dt = \frac{R_c}{R_{ref}} \int v_{ab} dt + \int v_{cd} dt. \qquad (eq.\ 11)$$

For periodic time-varying excitation $v_{cd}$, limits $l_1$, $l_2$ can be chosen such that $$\int_{l_1}^{l_2} v_{cd} dt = 0. \qquad (eq.\ 12)$$

By way of example, $l_1$ and $l_2$ may have values:

$$l_1 = -\frac{\pi}{2\omega},\ l_2 = \frac{\pi}{2\omega}$$

where $\omega$ is the angular frequency of the driving signal and the times $l_1$ and $l_2$ are measured with reference to the instant of zero crossover for the signal $v_{cd}$. It will be observed that the voltage $v_{cd}$ may not be measured, but it is known to be 90 degrees out of phase with $v_{ab}$. Therefore, the limits $l_1$ and $l_2$ may be set with respect to the peak value of $v_{ab}$, in which case they are equal to zero-crossings of $v_{ab}$.

Then, substituting eq. 12 in eq. 11 and solving for $R_c$ $$R_c = R_{ref} \frac{\int_{l_1}^{l_2} v_{bd} dt}{\int_{l_1}^{l_2} v_{ab} dt}. \qquad (eq.\ 13)$$

Thus, the unknown resistance $R_c$ can be found by multiplying the value of the reference resistance by the ratio of the integral of the sampled cell voltage to the integral of the sampled reference voltage. The value of the unknown resistance $R_c$ can thereby be found despite the presence of unknown series capacitance $C_s$. However, it should be noted that $l_2 - l_1$ may not have a value of $2\pi/\omega$, because such a condition causes Equation 13 to become indeterminate.

Figure 4:
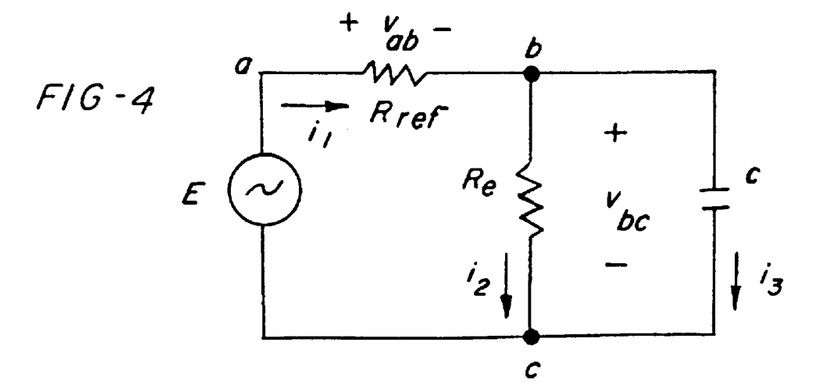
FIG. 4 is an electrical schematic of a conductivity measuring circuit modeled as a parallel circuit.

Similarly, for the parallel capacitance model shown in FIG. 4, the inventor has observed that $$v_{ab} = i_1 R_{ref} = R_{ref}(i_2 + i_3) \qquad (eq.\ 14)$$

and $$v_{bc} = i_2 R_c. \qquad (eq.\ 15)$$

Integrating both sides of equations 14 and 15 yields $$\int v_{ab} dt = R_{ref} \int i_2 dt + R_{ref} \int i_3 dt \qquad (eq.\ 16)$$

and $$\int v_{bc} dt = R_c \int i_2 dt. \qquad (eq.\ 17)$$

Solving eq. 17 for $\int i_2 dt$ and substituting the result in eq. 16 gives $$\int v_{ab} dt = \frac{R_{ref}}{R_c} \int v_{bc} dt + R_{ref} \int i_3 dt. \qquad (eq.\ 18)$$

For a periodic time-varying excitation $v_{ac}$, $i_3$ is also periodic and limits $l_3$, $l_4$ can be chosen such that $$\int_{l_3}^{l_4} i_3 dt = 0. \qquad (eq.\ 19)$$

By way of example, $l_3$ and $l_4$ may have values:

$$l_3 = -\frac{\pi}{2\omega},\ l_4 = \frac{\pi}{2\omega}$$

where $\omega$ is the angular frequency of the driving signal and the times $l_3$ and $l_4$ are measured with reference to the instant of zero crossover for the signal $i_3$. It will be observed that the current $i_3$ may not be measured, but it is known to be 90 degrees out of phase with current $i_2$ and voltage $v_{bc}$. Therefore, the limits $l_3$ and $l_4$ may be set with respect to the peak value of $v_{bc}$, in which case they are equal to zero-crossings of $v_{bc}$.

Substituting eq. 19 into eq. 18 and solving for $R_c$ yields $$R_c = R_{ref} \frac{\int_{l_3}^{l_4} v_{bc} dt}{\int_{l_3}^{l_4} v_{ab} dt}. \qquad (eq.\ 20)$$

Note the similarity of eq. 20 to eq. 13. Thus, the unknown resistance $R_c$ can be found by multiplying the value of the reference resistance $R_{ref}$ by the ratio of the integral of the sampled cell voltage $v_{bc}$ to the integral of the sampled reference voltage $v_{ab}$. The value of the unknown resistance $R_c$ can thereby be found despite the presence of unknown parallel capacitance $C_p$. However, it should be noted that $l_4 - l_3$ may not have a value of $2\pi/\omega$, because such a condition causes Equation 20 to become indeterminate.

It can be shown that the ratio of the integrals given in Equations 13 and 20 is equal to the ratio of the peak voltages divided by the cosine of the phase angle between the two voltage signals being monitored. Thus, if the peak voltage ratio is determined and is divided by the ratio of the integrals, it becomes possible to determine the phase angle and hence the value of the unknown capacitance.

Figure 5:
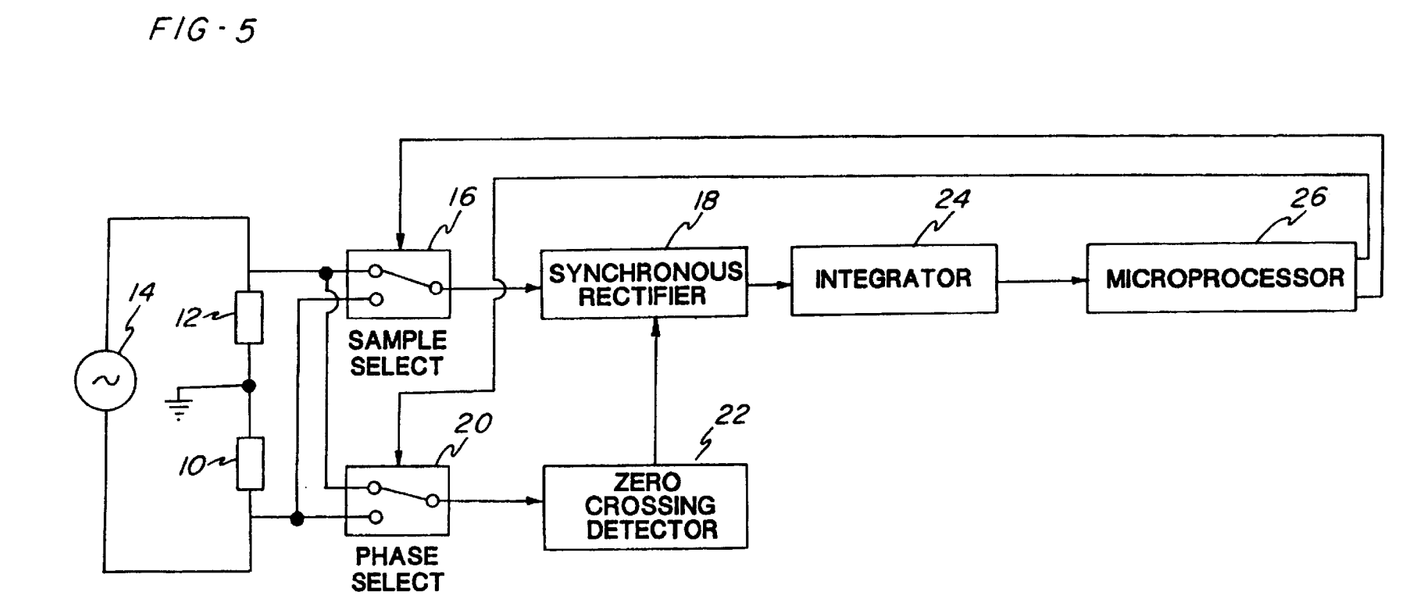
FIG. 5 is a block diagram of a conductivity measuring circuit.

Turning now to an examination of an apparatus which compensates for unknown capacitance when measuring unknown resistance, FIG. 5 shows a simplified block diagram of a circuit according to one embodiment of the invention. A liquid (not shown), the conductivity of which is to be measured, is disposed between electrodes (not shown) in a cell 10. Connected to one electrode of the cell 10 is a reference resistance 12. A sinusoidal voltage driving source 14 is connected across the reference resistance 12 and the cell 10 to form a series electrical circuit.

A sample signal select switch 16, controlled by a microprocessor 26, is connected so as to be able to connect either the voltage across the reference resistance 12, or the voltage across the cell 10, depending upon which signal voltage is to be sampled, to a synchronous rectifier 18. A phase signal select switch 20, controlled by the microprocessor 26, is connected so as to be able to connect either the voltage across the reference resistance 12, or the voltage across the cell 10, depending upon which signal voltage is to be the input to a zero-crossing detector 22.

The zero-crossing detector 22 provides a zero-crossing detect signal to the synchronous rectifier 18 each time the input signal to the zero-crossing detector 22 passes through zero Volts. Preferably, the synchronous rectifier 18 provides, at its output, in response to the zero-crossing detect signal, a non-inverted version of the sample signal at its input whenever the input voltage to the zero-crossing detector 22 is positive. When the input voltage to the zero-crossing detector 22 is negative, the synchronous rectifier 18 preferably provides at its output an inverted version of the sample signal at its input. Alternatively, the polarity of the output from synchronous rectifier 18 may be reversed without affecting the conductivity measurement. Then, when the input voltage to zero-crossing detector 22 is positive, the output from rectifier 18 is an inverted version of its input, while when the input voltage to detector 22 is negative, the output from rectifier 18 is a non-inverted version of its input.

The output of the synchronous rectifier 18 is provided to the input of an integrator 24. The integrator 24 produces a DC output voltage which is representative of the RMS value of the input voltage. The output of the integrator 24 is provided to the microprocessor 26 which calculates the value of the cell resistance by multiplying the value of the reference resistance 12 times the ratio of the integrated synchronously-rectified sampled cell voltage to the integrated synchronously-rectified sampled reference resistance voltage.

Thus, the zero-crossing detector 22 supplies the proper limits of integration so as to compensate for the effects of unknown capacitance present in combination with the unknown resistance being measured.

Figure 6:
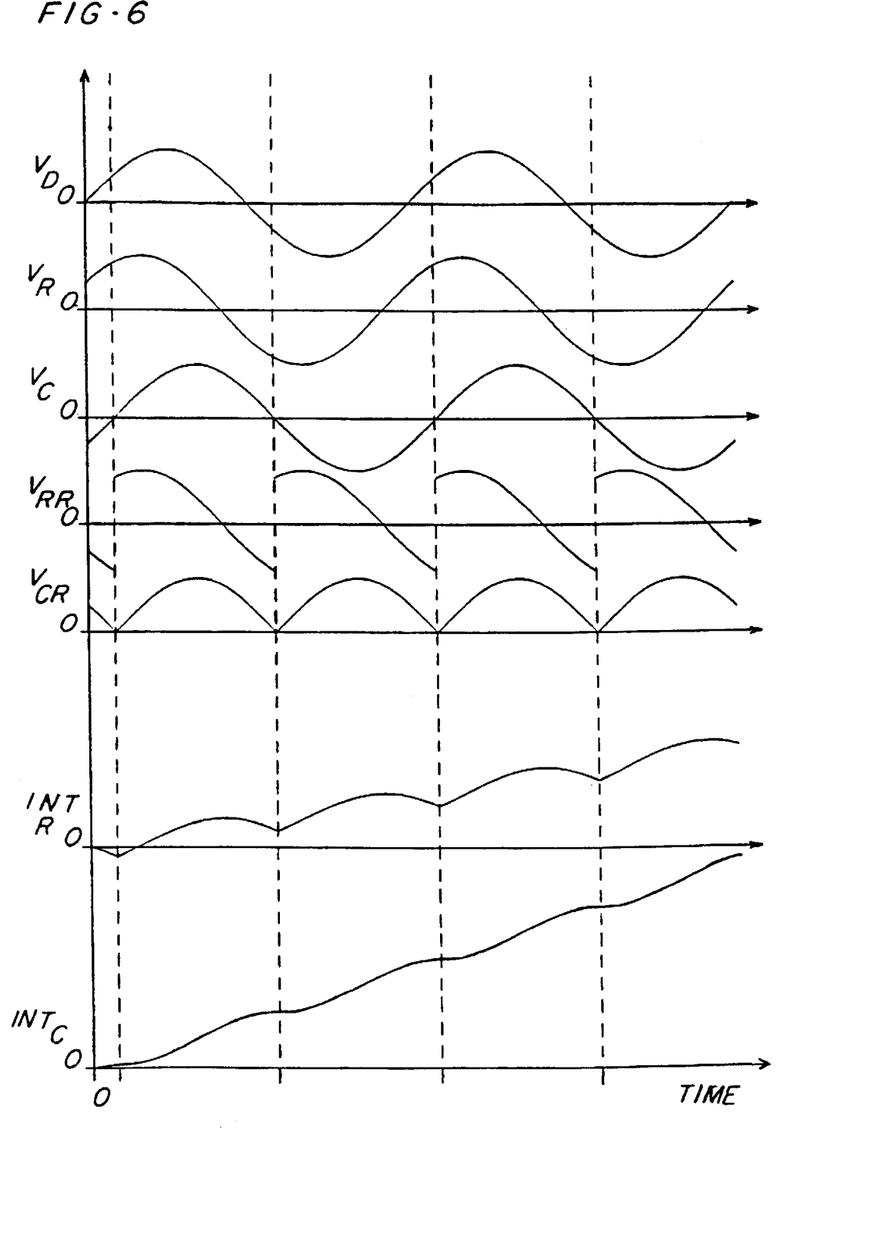
FIG. 6 is a set of electrical waveforms illustrating the operation of a conductivity measuring circuit.

The operation of the synchronous rectifier 18 may be more clearly understood by referring to the voltage waveforms shown in FIG. 6. The waveforms share a common vertical axis which represents voltage. The horizontal axes represent time. Voltage $V_D$ represents the driving voltage from signal source 14. Voltage $V_R$ represents the sampled voltage from reference resistor 12. Voltage $V_C$ represents the sampled cell voltage from cell 10. For the sake of clarity, all three voltages $V_D$, $V_C$, and $V_R$ are shown as having equal amplitude. Also, $V_R$ is shown with a phase angle of 30 degrees with respect to $V_D$, and $V_C$ is shown with a phase angle of −30 degrees with respect to $V_D$.

To illustrate the case where the resistivity is high and it is desired to remove the effects of parallel capacitance, synchronous rectification with respect to cell voltage $V_C$ is shown. Voltage $V_{CR}$ is the output of the synchronous rectifier 18 when $V_C$ is the input to synchronous rectifier 18 and zero-crossing detector 22. The vertical dashed lines in FIG. 6 show the timing relationship of the voltage waveforms with respect to the zero crossings of $V_C$. As can be seen, $V_{CR}$ is a full-wave rectified version of $V_C$.

Voltage $V_{RR}$ is the output of synchronous rectifier 18 when $V_R$ is the input to the synchronous rectifier 18 and $V_C$ is the input to the zero-crossing detector 22. During the time between zero crossings of $V_C$ when $V_C$ is positive, $V_{RR}$ is a non-inverted version of $V_R$. However, during the time between zero crossings of $V_C$ when $V_C$ is negative, $V_{RR}$ is an inverted version of $V_R$. Thus, $V_R$ is synchronously rectified with respect to $V_C$.

Voltage $INT_R$ represents the output of integrator 24 when the input is $V_{RR}$. Voltage $INT_C$ represents the output of integrator 24 when the input is $V_{CR}$. Because $V_{CR}$ is always a non-negative voltage, $INT_C$ steadily increases over time as additional cycles of $V_{CR}$ are integrated. Because $V_{RR}$ may be negative, $INT_R$ may show dips in amplitude at the zero crossings of $V_C$. If $V_R$ were exactly in phase with $V_C$, then $V_{RR}$ would match $V_{CR}$, and $INT_R$ would match $INT_C$. At the other extreme, if $V_R$ were exactly 90 degrees out of phase with $V_C$, then $INT_R$ would dip to zero at the zero crossings of $V_C$.

Thus, while the in-phase portion of $V_R$ due to current through the cell resistance integrates to some positive value, the 90 degree out-of-phase portion of $V_R$ due to current through the cell parallel capacitance integrates to a zero value. For the case of series cell capacitance, the same principles may be demonstrated by exchanging the voltages and viewing $V_R$ as the sampled cell voltage, $V_C$ as the sampled reference resistance voltage, $V_{RR}$ as the synchronously rectified cell voltage, $V_{CR}$ as the synchronously rectified reference voltage, $INT_R$ as the integrated cell voltage, and $INT_C$ as the integrated reference voltage.

Figure 7A:
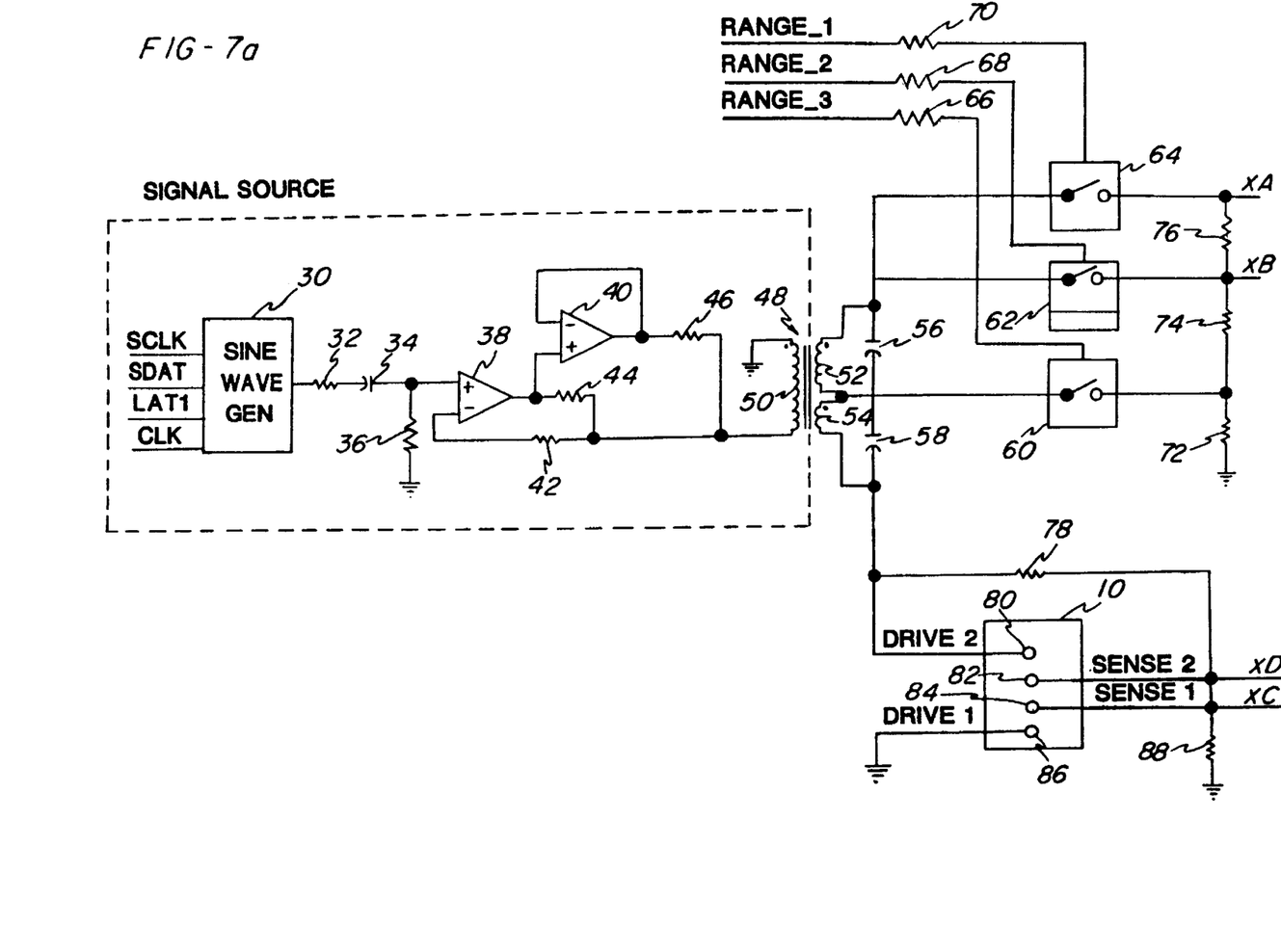
FIGS. 7a, 7b, and 7c are a detailed circuit schematic diagram of a preferred embodiment of the invention.
Figure 7B:
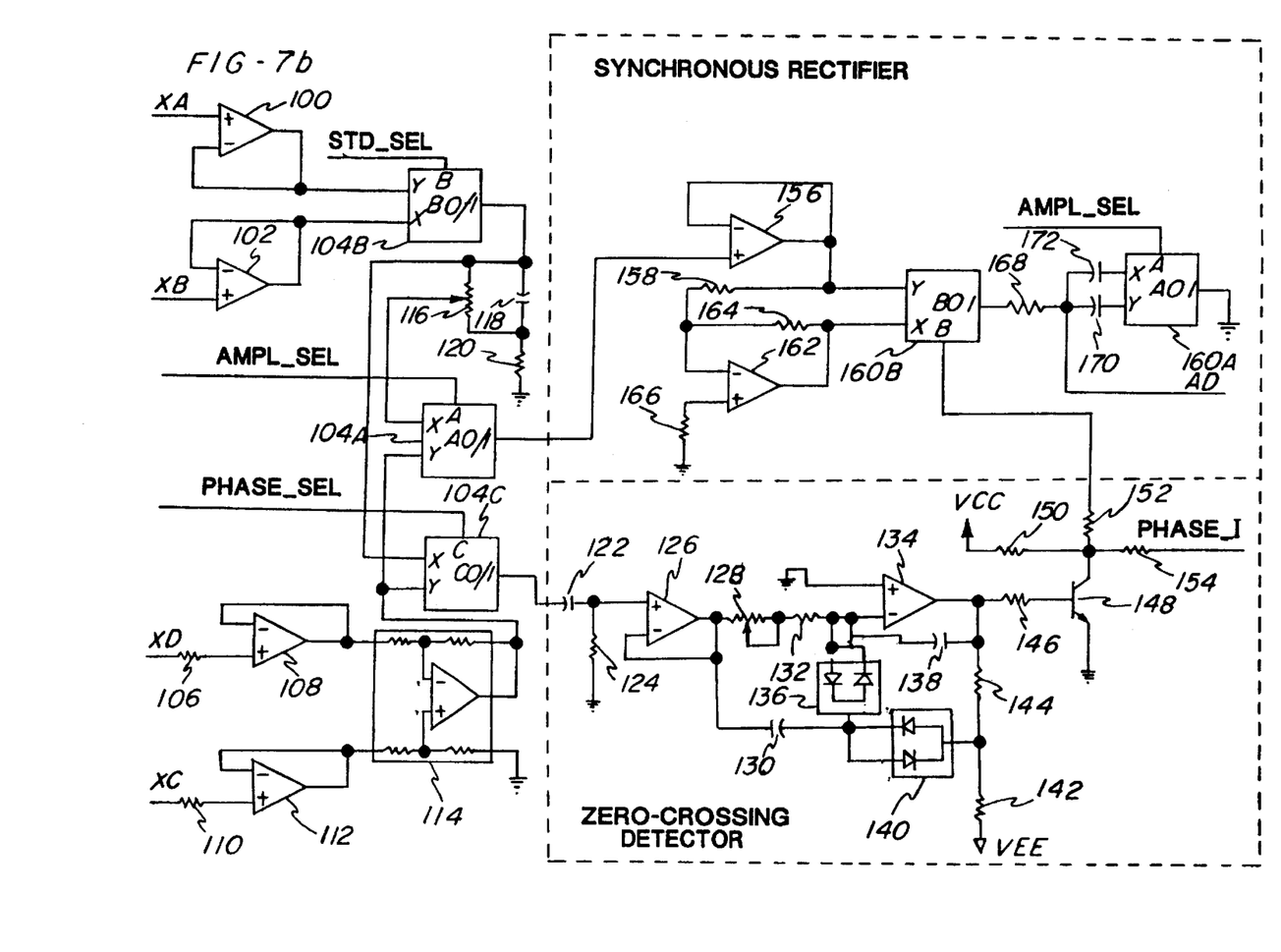
Figure 7C:
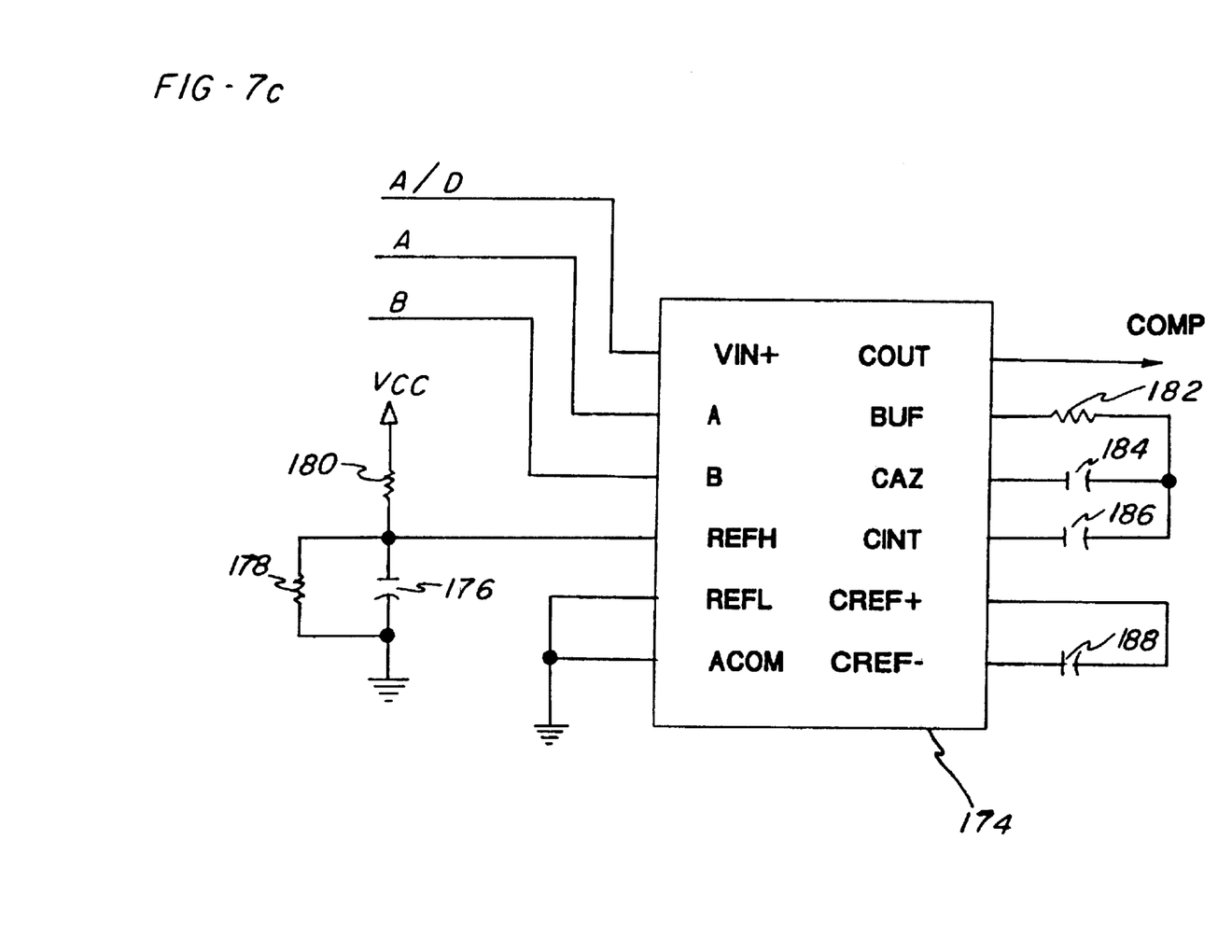

FIGS. 7a, 7b, and 7c show a preferred embodiment of the present invention. A programmable sine-wave generator 30 receives inputs from the microprocessor 26 (FIG. 5) and produces a sine-wave output of fixed amplitude. One such programmable sine-wave generator 30 is the Micro Linear ML2035, which is programmable from DC to 25 kHz. The sine-wave generator 30 provides a highly stable source of sine-wave excitation at a frequency determined by the inputs from the microprocessor.

The output of sine-wave generator 30 passes through series-limiting resistor 32 and DC-blocking capacitor 34 to resistor 36 and the non-inverting input of op amp 38. Op amps 38 and 40, and resistors 42, 44, and 46, buffer the sine-wave signal and provide sufficient current to drive a primary winding 50 of isolation transformer 48. The sine-wave input to isolation transformer 48 is inductively coupled to two secondary windings 52 and 54 of the transformer 48.

The secondary windings 52, 54 are series-connected. Capacitors 56 and 58 are series-connected across the output of secondary windings 52, 54. The common tap of windings 52, 54 is connected to switch 60. The other tap of winding 52 is connected to switches 62 and 64. Range selection signals RANGE_1, RANGE_2, and RANGE_3, from the microprocessor 26 (FIG. 5), pass through series-limiting resistors 66, 68, and 70, to switches 60, 62, and 64, respectively. Reference resistors 72, 74, and 76 are connected in series with one end of resistor 72 tied to ground. The output of switch 60 is connected to the common tie point of resistors 72 and 74. The output of switch 62 is connected to the common tie point of resistors 74 and 76. The output of switch 64 is connected to the other lead of resistor 76.

In response to range selection signals RANGE_1, RANGE_2 and RANGE_3, from the microprocessor 26 (FIG. 5), the switches 60, 62, 64 may be turned on or off. A low range selection signal turns a switch on while a high range selection signal turns a switch off. When turned on, the switches 60, 62, 64 have very low resistance and couple the sine-wave signal from one of the windings 52, 54 to the reference resistors 72, 74, 76. When the switches 60, 62, 64 are off, they exhibit very high input impedance to provide isolation between the inputs to the switches 60, 62, 64 and the reference resistors 72, 74, 76. Switches which may be used for this purpose are Photo-MOS relay switches made by Aromat. Switches 62, 64 may be Aromat AQV210EA switches which typically exhibit $10^{10}\Omega$ off resistance and 30–100Ω on resistance. Switch 60 may be an Aromat AQV215A which typically exhibits $10^8\Omega$ off resistance and about 5Ω on resistance.

Resistors 72, 74, and 76 preferably are precision resistors that exhibit superior stability over time and a wide range of operating conditions. Values for resistors 72, 74 and 76 preferably are 10Ω, 1 kΩ, and 100 kΩ. Preferably, resistor 72 will have the smallest value and resistor 76 will have the largest value.

In operation, when the resistance being measured is small, RANGE_3 is low, RANGE_1 and RANGE_2 are high, switch 60 is on, switches 62 and 64 are off, and sine-wave excitation is coupled from the common tie point of windings 52 and 54 to the common tie point of resistors 72 and 74. When the resistance being measured is of some intermediate value, RANGE_2 is low, RANGE_1 and RANGE_3 are high, switch 62 is on, switches 60 and 64 are off, and sine-wave excitation is coupled from winding 52 to the common tie point of resistors 74 and 76. When the resistance being measured is large, RANGE_1 is low, RANGE_2 and RANGE_3 are high, switch 64 is on, switches 60 and 62 are off, and sine-wave excitation is coupled from winding 52 to resistor 76.

Secondary winding 54 is further connected to cell 10 and resistor 78. Preferably, cell 10 is a four-wire, four-element cell. Alternatively, cell 10 may be a four-wire, two-element cell. A four-wire, four-element cell 10 has electrodes 80, 82, 84, and 86. Electrodes 80 and 86 are drive electrodes and receive the sine-wave excitation from winding 54. Electrode 80 is the DRIVE2 input and is connected to winding 54, while electrode 86 is the DRIVE1 input and is tied to ground to complete a drive circuit path through cell 10. Electrodes 82 and 84 are sense electrodes to detect the voltage across and the current through cell 10. Electrode 82 is the SENSE2 electrode, while electrode 84 is the SENSE1 electrode. Resistor 78 is connected between DRIVE2 electrode 80 and SENSE2 electrode 82, while resistor 88 is connected between SENSE1 electrode 84 of cell 10 and ground. Resistors 78 and 88 preferably are of equal value and act to keep circuit parameters stable when cell 10 is disconnected from the circuit.

In a typical four-wire, four-element cell, an excitation is applied to drive electrodes 80 and 86. Sense electrode 82 is positioned sufficiently close to drive electrode 80 so as to be substantially at the same electrical potential as drive electrode 80. Similarly, sense electrode 84 is positioned sufficiently close to drive electrode 86 so as to be substantially at the same electrical potential as drive electrode 86. Sense electrodes 82 and 84 are preferably disposed substantially within the current flow path through the cell 10 between drive electrodes 80 and 86. In a typical four-wire, two-element cell, drive electrode 80 is electrically short-circuited to sense electrode 82, and drive electrode 86 is electrically short-circuited to sense electrode 84.

In operation, a complete circuit path is traversed from one side of winding 52, through one of the switches 60, 62, and 64, through resistors 72, 74, and 76, to ground. From ground, the circuit path continues to electrode 86 of cell 10, through cell 10 to electrode 80, then through winding 54 to the other side of winding 52, thus completing the circuit path. The values of the range selection signals determine whether one, two, or all three of resistors 72, 74, and 76 are in the circuit path. Thus, it can be seen that, as shown in FIG. 5, the signal source 14, reference resistance 12, and cell 10 form a series circuit.

Turning to FIG. 7b, the tie point of switch 64 and resistor 76 (FIG. 7a) is connected to the non-inverting input of op amp 100, while the tie point of switch 62 and resistors 74 and 76 (FIG. 7a) is connected to the non-inverting input of op amp 102. Op amps 100 and 102 are unity-gain buffer amplifiers that buffer the voltages XA, XB, respectively, from the reference resistors 72, 74, and 76 (FIG. 7a). The outputs of op amps 100 and 102 are connected to inputs Y and X, respectively, of analog switch 104B. Switch 104B is one of three switches, along with switches 104A and 104C, contained in a single integrated circuit package. A preferred analog switch that features low sine-wave distortion and low crosstalk between switches is the HC4053 triple 2-channel analog multiplexer/demultiplexer made by SGS-Thomson Microelectronics.

From the microprocessor 26 (FIG. 5), a standard select signal, STD_SEL, is connected to input B of switch 104B. The value of STD_SEL determines which input, X or Y, is connected to output BO/I. When RANGE_1 is low and switch 64 (FIG. 7a) is on, then STD_SEL is high, input Y is connected to output BO/I, and reference resistance voltage XA is present at output BO/I of switch 104B. When either RANGE_2 or RANGE_3 is low, then STD_SEL is low, input X is connected to output BO/I, and reference resistance voltage XB is present at output BO/I of switch 104B.

The tie point of electrode 82 and resistor 78 (FIG. 7a) is connected, through series-limiting resistor 106, to the non-inverting input of unity-gain buffer op amp 108. The tie point of electrode 84 and resistor 88 is connected, through series-limiting resistor 110, to the non-inverting input of unity-gain buffer op amp 112. The output of op amp 108 is connected to the inverting input of unity-gain differential amplifier 114, while the output of op amp 112 is connected to the non-inverting input of unity-gain differential amplifier 114.

In the preferred embodiment, differential amplifier 114 is a Precision Monolithics AMP-03 is used due to its high (70–80 dB) common-mode rejection ratio ("CMRR"). The unity-gain differential amplifier 114 eliminates common mode voltages from the cell sense potentials XC and XD. For low unknown resistances, the resistance in the lead wires going to and from the cell 10 (FIG. 7a) may be sufficiently large relative to the cell resistance so as to induce relatively large measurement errors. Using four lead wires to the cell, in combination with unity-gain differential amplifier 114, effectively eliminates lead wire resistance as a source of measurement error.

The output of unity-gain differential amplifier 114 is connected to input Y of switch 104A and input Y of switch 104C. Output BO/I of switch 104B is connected to potentiometer 116, capacitor 118, and input X of switch 104C. The wiper arm of potentiometer 116 is connected to input X of switch 104A. Potentiometer 116, capacitor 118, and resistor 120 form a low-frequency compensation circuit Potentiometer 116 may be adjusted to ensure that zero crossings are accurately detected for low frequency sine-wave excitations.

From the microprocessor 26 (FIG. 5), a phase select signal, PHASE_SEL, is connected to input C of switch 104C, and determines whether input X or Y is connected to output CO/I of switch 104C. When the unknown cell resistance is high, PHASE_SEL is high, input Y of switch 104C is connected to output CO/I so that the sampled cell voltage at the output of differential amplifier 114 appears at output CO/I of switch 104C, and synchronous rectification takes place with respect to the cell voltage to eliminate parallel capacitance effects. When the unknown cell resistance is low, PHASE_SEL is low, input X of switch 104C is connected to output CO/I so that the sampled reference resistance voltage at the output BO/I of switch 104B appears at the output CO/I of switch 104C, and synchronous rectification takes place with respect to the reference resistance voltage to eliminate series capacitance effects.

Also from the microprocessor 26 (FIG. 5), an amplitude select signal, AMPL_SEL, is connected to input A of switch 104A, and determines whether input X or Y is connected to output AO/I of switch 104A. When it is desired to integrate the sampled reference resistance voltage, then AMPL_SEL is low, input X of switch 104A is connected to output AO/I, and the sampled reference resistance voltage at output BO/I of switch 104B is present at output AO/I of switch 104A. When it is desired to integrate the sampled cell voltage, then AMPL_SEL is high, input Y of switch 104A is connected to output AO/I, and the sampled cell voltage at the output of differential amplifier 114 is present at output AO/I of switch 104A

Output CO/I of switch 104C is connected to capacitor 122. Capacitor 122 is a DC blocking capacitor that couples the sampled voltage which is to be used as the phase synchronization reference to resistor 124 and the non-inverting input of op amp 126. Op amp 126 is a unity-gain buffer amplifier that couples the signal to potentiometer 128 and capacitor 130. Potentiometer 128 is in turn connected to resistor 132. The signal is then coupled from resistor 132 to the inverting input of op amp 134, back-to-back diode 136, and capacitor 138.

Capacitor 130 is further connected to back-to-back diodes 136 and 140. Back-to-back diode 140 is then connected to resistors 142 and 144. The other lead of resistor 142 is tied to $V_{EE}$, the negative supply voltage. The other lead of resistor 144 is connected to the output of op amp 134 and capacitor 138. The non-inverting input of op amp 134 is tied to ground. The output of op amp 134 is further connected to series-limiting resistor 146. Series-limiting resistor 146 couples the output from op amp 134 to the base of transistor 148. Transistor 148 is an NPN-type transistor with input to the base, emitter tied to ground, and output at the collector. The output at the collector is an inverted and amplified version of the signal input to the base. The collector of transistor 148 is connected to resistors 150, 152, and 154. The other lead of resistor 150 is tied to $V_{CC}$, the positive supply voltage, and provides collector current to transistor 148. The output of transistor 148 is the zero-crossing signal PHASE_I. PHASE_I is a square wave signal in phase with the sine-wave input to the zero-crossing detector 22 (FIG. 5) and has amplitude from about zero Volts to about five Volts.

Capacitors 122, 130, and 138, resistors 124, 128, 132, 144, 142, 146, 150, 152, and 154, op amps 126 and 134, back-to-back diodes 136 and 140, and transistor 148 collectively comprise the zero-crossing detector 22 (FIG. 5). In the preferred embodiment, the op amps 126 and 134 are MC34182 op amps, the back-to-back diodes 136 and 140 are MMBD7000L diodes, and transistor 148 is an MMBT3904LT1 general-purpose NPN silicon transistor, all manufactured by Motorola, Inc.

The signal that supplies the reference phase is coupled into the detector 22 (FIG. 5) through blocking capacitor 122 and buffer op amp 126. The input to detector 22 is typically a sine-wave voltage of from about 50 m $V_{RMS}$ to about 2.0 $V_{RMS}$. The signal is then coupled through potentiometer 128 and resistor 132 to the inverting input of op amp 134. The signal level at the inverting input of op amp 134 is compared to the ground level at the non-inverting input of op amp 134 and the difference is amplified. Because of the large open-loop gain of op amp 134, the output of op amp 134 is driven toward $V_{CC}$ when the input signal is negative, and toward $V_{EE}$ when the input signal is positive. Thus, for a sine-wave input, the output of op amp 134 is an inverted square wave.

Resistors 142 and 144 provide the proper DC level at the output of op amp 134 and proper DC bias for back-to-back diodes 136 and 140. To prevent op amp 134 from being driven into saturation, back-to-back diodes 136 and 140 provide feedback from the output of op amp 134 to the inverting input of op amp 134 so as to cause op amp 134 to operate in current mode, thereby limiting the gain of op amp 134. The values of resistors 142 and 144 preferably are such that the output of op amp 134 is a square wave of amplitude from about −0.5V to about +1.5V with midpoint about equal to the forward conductance voltage $V_{BE}$ of transistor 148.

Capacitor 138 provides feedback from the output of op amp 134 to the inverting input of op amp 134 to ensure more stable switching of the op amp 134 output for input voltage levels substantially equal to zero volts by damping high-frequency oscillations at the output of op amp 134. Capacitor 130 provides a small amount of leading phase angle to compensate for a small amount of lagging phase angle induced by off-state capacitance of the back-to-back diodes 136 and 140. Resistor 132 provides series current limiting of the input signal to op amp 134 while potentiometer 128 provides a means for compensating the phase angle of high-frequency input signals for small zero-crossing detection errors.

Output AO/I of switch 104A is connected to the non-inverting input of unity-gain buffer op amp 156. The output of op amp 156 is connected to resistor 158 and input Y of analog switch 160B. In the preferred embodiment, switch 160B is one switch of an HC4053 triple 2-channel analog multiplexer/demultiplexer manufactured by SGS-Thomson Microelectronics. Op amp 162, resistors 158, 164, and 166 comprise a unity-gain inverting amplifier such that the voltage waveform at the output of op amp 162 is a mirror-image of the voltage waveform at the output of op amp 156. Preferably, resistors 158 and 164 are precision resistors of equal value, and resistor 166 has value approximately half that of resistors 158 and 164. The output of op amp 162 is connected to input X of switch 160B. The output of transistor 148 is coupled through series-limiting resistor 152 to input B of switch 160B.

Input B of switch 160B determines whether input X or input Y is connected to output BO/I. When the input to zero-crossing detector 22 (FIG. 5) is positive, PHASE_I is high, input Y of switch 160B is connected to output BO/I, and the non-inverted version of the input voltage to the synchronous rectifier 18 (FIG. 5) is present at the output BO/I of switch 160B. When the input to zero-crossing detector 22 is negative, PHASE_I is low, input X of switch 160B is connected to output BO/I, and the inverted version of the input voltage to the synchronous rectifier 18 is present at the output BO/I of switch 160B.

Output BO/I of switch 160B is connected to a switch-capacitor low-pass filter comprised of resistor 168 and capacitors 170 and 172. Capacitor 170 is connected to input Y of switch 160A, and capacitor 172 is connected to input X of switch 160A. Amplitude signal select line AMPL_SEL, from the microprocessor 26 (FIG. 5), is connected to input A of switch 160A. The signal AMPL_SEL determines whether capacitor 170 or 172 is connected to ground through output AO/I of switch 160A. When AMPL_SEL is low, input X of switch 160A is connected to output AO/I, and capacitor 172 is connected to ground. When AMPL_SEL is high, input Y of switch 160A is connected to output AO/I, and capacitor 170 is connected to ground. Thus, capacitor 170 is switched into the low-pass filter when the synchronously-rectified sampled cell voltage is being integrated, and capacitor 172 is switched into the low-pass filter when the synchronously-rectified sampled reference resistance voltage is being integrated. Using two separate capacitors 170 and 172 for filtering the output of synchronous rectifier 18 permits faster switching between input signals to the integrator 24 (FIG. 5).

The BO/I output of switch 160B passes through resistor 168 to the VIN+ input of integrating analog-to-digital converter 174 (FIG. 7c). Analog-to-digital converter 174, in the preferred embodiment, is a TC500A integrating converter analog processor manufactured by Teledyne Components. Converter 174 is a microprocessor-controlled dual-slope integrating converter. Capacitor 176 and resistors 178 and 180 provide a reference voltage to input REFH of converter 174. The reference voltage of the preferred embodiment is about 200 mV, but the absolute value is not critical so long as the voltage remains stable from one conversion to the next. Inputs REFL and ACOM are tied to ground. Connected to input BUF is resistor 182. Capacitor 184 is connected to input CAZ and capacitor 186 is connected to input CINT. The other ends of resistor 182 and capacitors 184 and 186 are tied together. Capacitor 188 is connected between inputs CREF+ and CREF−. From the microprocessor 26 (FIG. 5), two control signals, A and B, are connected to inputs A and B, respectively. The output of the converter 174 appears at output COUT as output signal COMP.

When the control signals AB to converter 174 are set to 01, converter 174 is in its resting state (i.e. not converting). On instruction from the microprocessor 26, control signals AB are set to 10 to begin the integration process. Integration is set to begin and end on zero crossings detected by the zero-crossing detector 22 (FIG. 5), with a minimum integration time as determined by the microprocessor 26 such that an even number of half-cycles will always be integrated. Integrating over an even number of half-cycles helps to eliminate error due to possible DC levels present in the signal to be integrated. Also, to enhance resolution of low voltage signals, the integration time may be lengthened. During the signal integration period, the microprocessor 26 counts the number of microprocessor clock cycles to determine the actual integration time.

At the end of the signal integration period, microprocessor 26 sets control signals AB to 11 to start deintegration. Converter 174 then integrates the reference voltage at input REFH so as to drive the output at COUT back toward zero. The microprocessor 26 counts microprocessor clock cycles during the deintegration period. When the COMP output signal goes low, deintegration is complete, and the microprocessor 26 sets control signals AB to 01 to zero the converter 174 COMP output until the next conversion period.

The microprocessor 26 then uses the integration time, deintegration time, and known reference voltage to compute a DC voltage value for the signal voltage applied to the converter 174 VIN+ input during the integration time period. The larger the input voltage to converter 174 is relative to the reference voltage at VREF+, the longer it takes to deintegrate the COMP output back to a low level. The computed DC voltage value represents the RMS voltage value for the input voltage and is computed by multiplying the known reference voltage times the ratio of the deintegration time to the integration time.

Figure 8:
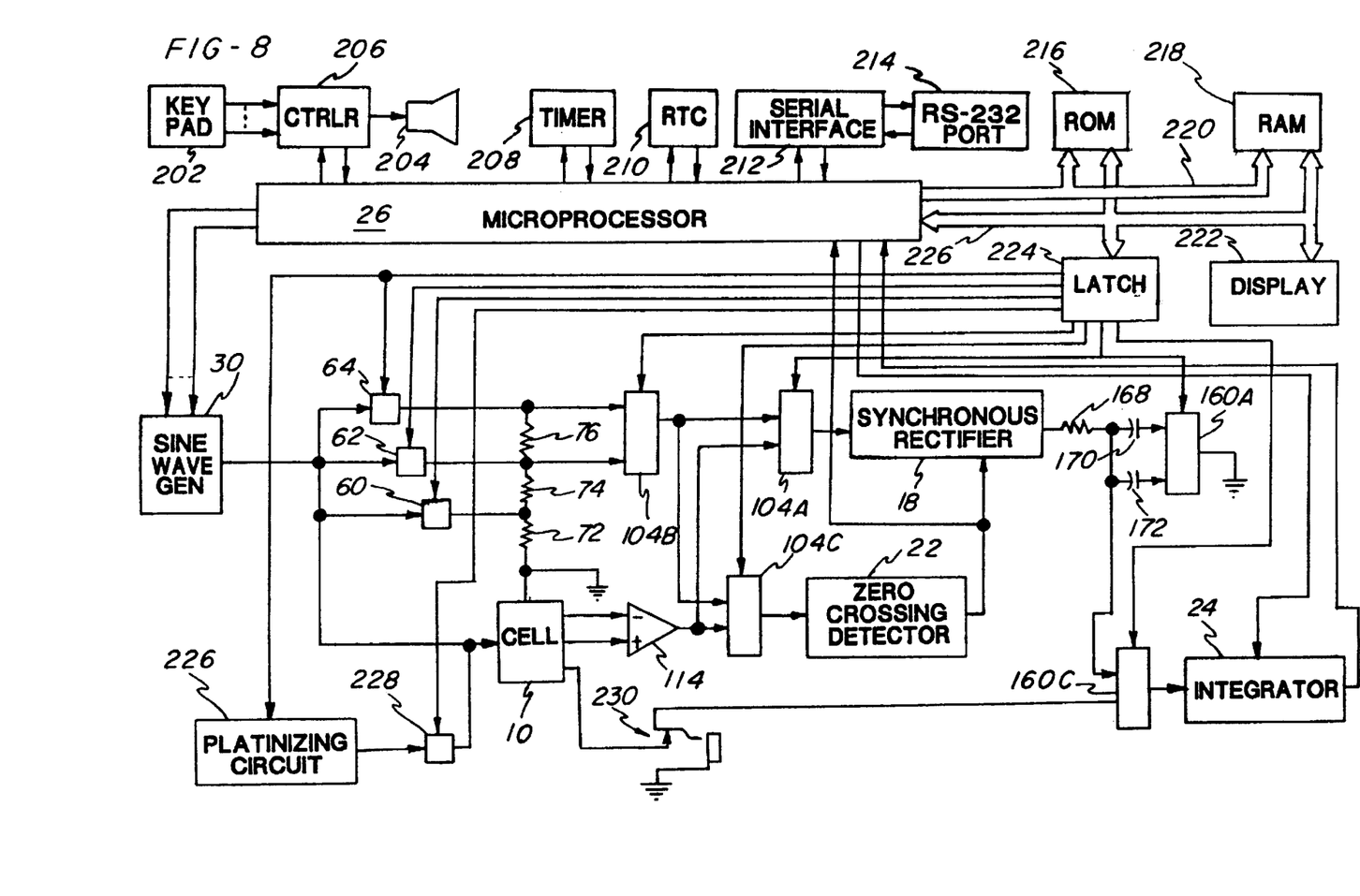
FIG. 8 is a block diagram of a conductivity meter incorporating the present invention.

Turning now to FIG. 8, a conductivity meter incorporating the preferred embodiment of the invention can be seen. Microprocessor 26 is connected to a keypad 202 and buzzer 204 through keypad controller 206. An operator can enter information into the meter and select different modes of operation through keypad 202. The microprocessor 26 can generate a tone from buzzer 204 when desired. Watchdog timer 208 monitors microprocessor 26 and provides a reset signal to microprocessor 26 if no microprocessor 26 activity is detected for a predetermined interval of time. Real time clock 210 provides external timing information to microprocessor 26. Microprocessor 26 is connected through serial port interface 212 to an RS-232 port 214 to permit communication with external peripheral devices. Programmable read-only memory ("ROM") 216 contains the software instructions which control the operation of the meter and are executed by microprocessor 26. Random-access memory ("RAM") 218 is used by microprocessor 26 to store information Microprocessor 26 addresses ROM 216 and RAM 218 via address bus 220. Data is communicated among the microprocessor 26, ROM 216, RAM 218, display 222, and data latch 224 via data bus 226. Display 222 is preferably a liquid-crystal display, but may be any means suitable for visually displaying information. Data latch 224 holds the various control signals used by the different parts of the meter.

Microprocessor 26 controls the operation of sine-wave generator 30 to produce sine-wave excitation of predetermined frequency and amplitude. Sine-wave excitation is coupled by means of switches 64, 62, and 60, in response to range select signals RANGE_1, RANGE_2, and RANGE_3, respectively, from data latch 224, to reference resistors 76, 74, and 72. Sine-wave excitation is also coupled from sine-wave generator 30 to cell 10. Range select signal RANGE_1 is also coupled to platinizing circuit 226, which is coupled to cell 10 via switch 228 in response to a platinizing signal PLAT from data latch 224. Platinizing circuit 226 provides a reversible 30 mA current to cell 10 to permit deposition of platinum black on the cell electrodes (not shown).

In response to standard select signal STD_SEL from latch 224, switch 104B provides the appropriate reference resistance sample voltage to switches 104A and 104C. The sampled cell voltages from cell 10 are applied to differential amplifier 114, then to switches 104A and 104C. In response to phase select signal PHASE_SEL from latch 224, switch 104C passes the appropriate sample voltage to zero-crossing detector 22. The zero-crossing detector 22 output signal PHASE_I is provided to microprocessor 26 and synchronous rectifier 18.

In response to amplitude select signal AMPL_SEL, switch 104A passes the appropriate sample voltage to synchronous rectifier 18. The synchronously-rectified output from rectifier 18 is coupled to the switched-capacitor low-pass filter comprised of resistor 168 and capacitors 170 and 172. The appropriate capacitor 170 or 172 is connected to ground by switch 160A in response to signal AMPL_SEL from latch 224.

Cell 10 may contain a built-in thermistor (not shown) which provides an output through external thermistor jack 230 to switch 160C. Temperature information from the built-in thermistor, or alternatively from an external thermistor (not shown), is coupled from jack 230 to switch 160. In response to a signal A/D__SEL from latch 224, switch 160 passes either a synchronously-rectified sample voltage or a thermistor voltage to integrator 24. The output from integrator 24 is provided to microprocessor 26 for calculation of the appropriate parameters.

Although the present invention has been described with reference to preferred embodiments, it is to be understood that various modifications may be made without departing from the spirit and scope of the invention. Moreover, the invention is not limited to the particular form or arrangement described herein except to the extent that such limitations are found in the claims.

What is claimed is:

1. A method of compensating for unknown parallel capacitance during measurement of the resistivity of a liquid, comprising the steps of:

(1) placing said liquid in communication with a pair of cell electrodes;

(2) placing a reference resistance in series with said cell electrodes;

(3) connecting a periodic, alternating electrical drive potential across the series combination of said cell electrodes and said reference resistance;

(4) measuring a potential difference across said cell electrodes;

(5) determining a first crossover time at which said potential difference across said cell electrodes undergoes a first change of sign between a negative and a positive value;

(6) determining a second crossover time when said potential difference across said cell electrodes undergoes another change of sign between a negative and a positive value;

(7) measuring a potential difference across said reference resistance;

(8) generating a reference integrand by integrating said potential difference across said reference resistance for a time period extending from said first crossover time to said second crossover time;

(9) generating a cell integrand by integrating said potential difference across said cell for a time period extending from said first crossover time to said second crossover time;

(10) calculating a ratio between said cell integrand and said reference integrand; and (11) multiplying said ratio by said reference resistance.

2. A method according to claim 1 wherein said periodic, alternating electrical drive potential is a sine wave.

3. A method according to claim 1 wherein said potential difference across said cell electrodes is rectified prior to integration thereof.

4. A method according to claim 1 wherein said potential difference across said reference resistance is rectified synchronously with respect to said potential difference across said cell electrodes prior to integration thereof.

5. A method of compensating for unknown series capacitance during measurement of the resistivity of a liquid, comprising the steps of:

(1) placing said liquid in communication with a pair of cell electrodes;

(2) placing a reference resistance in series with said cell electrodes;

(3) connecting a periodic, alternating electrical drive potential across the series combination of said cell electrodes and said reference resistance;

(4) measuring a potential difference across said reference resistance;

(5) determining a first crossover time at which said potential difference across said reference resistance undergoes a first change of sign between a negative and a positive value;

(6) determining a second crossover time when said potential difference across said reference resistance undergoes another change of sign between a negative and a positive value;

(7) measuring a potential difference across said cell electrodes;

(8) generating a reference integrand by integrating said potential difference across said reference resistance for a time period extending from said first crossover time to said second crossover time;

(9) generating a cell integrand by integrating said potential difference across said cell for a time period extending from said first crossover time to said second crossover time;

(10) calculating a ratio between said cell integrand and said reference integrand; and (11) multiplying said ratio by said reference resistance.

6. A method according to claim 5 wherein said periodic, alternating electrical drive potential is a sine wave.

7. A method according to claim 5 wherein said potential difference across said cell electrodes is rectified prior to integration thereof.

8. A method according to claim 5 wherein said potential difference across said reference resistance is rectified synchronously with respect to said potential difference across said cell electrodes prior to integration thereof.

9. Apparatus for measuring the resistivity of a liquid, said apparatus comprising:

(a) a pair of cell electrodes for contacting said liquid;

(b) a reference resistance connected in series with said cell electrodes;

(c) a driver for generating a periodic alternating drive signal and applying said drive signal to the series combination of said cell electrodes and said reference resistance;

(d) a sample selector for selectively generating either a cell sample signal or a reference resistance sample signal, said cell sample signal indicating the voltage across said cell electrodes and said reference resistance sample signal indicating the voltage across said reference resistance;

(e) a phase detector for selectively detecting either a cell phase indicating the phase of said cell sample signal or a reference resistance phase indicating the phase of said reference resistance sample signal;

(f) a synchronous rectifier for selectively rectifying either said reference resistance sample signal and said cell sample signal synchronously with respect to the phase of the reference resistance sample signal or, alternatively, rectifying said reference resistance sample signal and said cell sample signal synchronously with respect to the phase of said cell sample signal;

(g) an integrator for generating a first cell integrand by integrating said cell sample signal, a second cell integrand by integrating said synchronously rectified cell signal, a first reference resistance integrand by integrating said rectified reference resistance signal and a second reference resistance integrand by integrating said synchronously rectified reference resistance signal; and (h) a microprocessor for controlling the operation of said sample selector and said synchronous rectifier, said microprocessor also being programmed to calculate a resistivity value selectively compensated for unknown parallel capacitance by multiplying said reference resistance against a first ratio or alternatively compensated for an unknown series capacitance by multiplying said reference resistance against a second ratio, said first ratio being the ratio of said first cell integrand to said second reference resistance integrand, said second ratio being the ratio of said second cell integrand to said first reference resistance integrand.

* * * * *